United States Patent
Nakagome et al.

(10) Patent No.: US 6,329,551 B1
(45) Date of Patent: Dec. 11, 2001

(54) PHENYLENEDIAMINE DERIVATIVE, PRODUCTION METHOD THEREOF AND ANTIOXIDANT FOR RUBBER USING IT AS EFFECTIVE CONSTITUENT (75) Inventors: Seiji Nakagome; Akihiko Toda, both of Ibaraki-ken (JP)

(73) Assignee: NOK Corporation, Tokyo (JP)

( * ) Notice: Subject to any disclaimer, the term of this patent is extended or adjusted under 35 U.S.C. 154(b) by 0 days.

(21) Appl. No.: 09/544,208

(22) Filed: Apr. 7, 2000

Related U.S. Application Data (62) Division of application No. 09/106,457, filed on Jun. 30, 1998.

(30) Foreign Application Priority Data

Jul. 4, 1997 (JP) .................................................. 9-194921
Oct. 24, 1997 (JP) .................................................. 9-309867

(51) Int. Cl.$^7$ ................................................ C07C 211/00
(52) U.S. Cl. ........................ 564/330; 564/315; 564/331; 252/405; 558/415
(58) Field of Search ............................ 252/405; 564/315, 564/330, 331; 558/415

(56) References Cited

FOREIGN PATENT DOCUMENTS 0072575    2/1983   (EP) ..................................................

*Primary Examiner*—Samuel Barts
(74) *Attorney, Agent, or Firm*—Jacobson Holman, PLLC (57) ABSTRACT

A phenylenediamine derivative represented by following formula (I) or (II):

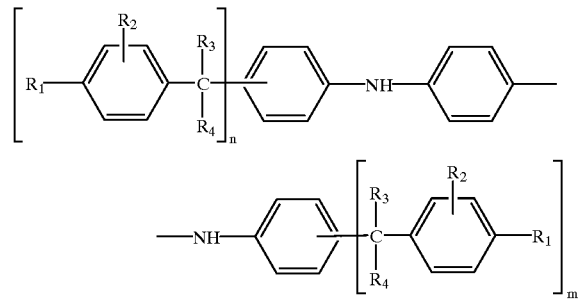

(I)

wherein $R_1$ and $R_2$ each represents a hydrogen atom, a lower alkyl group, or a lower alkoxy group; $R_3$ represents a hydrogen atom or a methyl group; $R_4$ represents a methyl group or an ethyl group; and n and m each is 1, 2, or 3;

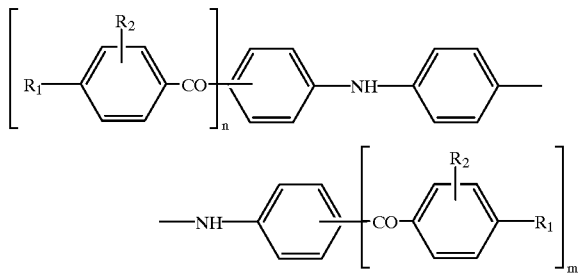

(II)

wherein $R_1$ and $R_2$ each represents a hydrogen atom, a lower alkyl group, a lower alkoxy group, or a cyano group; and n and m each is 1, 2, or 3, is disclosed.

These phenylenediamine derivatives are effectively used as antioxidants for rubbers, which scarcely cause vanishing by evaporation or a thermal denaturation even under a high-temperature condition of 150° C. or higher.

4 Claims, 4 Drawing Sheets

PHENYLENEDIAMINE DERIVATIVE, PRODUCTION METHOD THEREOF AND ANTIOXIDANT FOR RUBBER USING IT AS EFFECTIVE CONSTITUENT

This is a Divisional of application Ser. No. 09/106,457 filed Jun. 30, 1998.

FIELD OF THE INVENTION

The present invention relates to a phenylenediamine derivative, a production method thereof, and an antioxidant for rubber using the phenylenediamine derivative as the effective constituent. More specifically, the present invention relates to a phenylenediamine derivative which is stable at a high temperature of 150° C. or higher, a production method thereof, and an antioxidant for rubber using the phenylenediamine derivative as the effective constituent.

Also, the present invention relates to an antioxidant for acrylic rubbers. More specifically, the present invention relates to an antioxidant for acrylic rubbers capable of giving an excellent heat aging resistance to an acrylic rubber vulcanization product by using two kinds of antioxidant compounds.

BACKGROUND OF THE INVENTION

In particular, requirements for high temperature resistant materials or for longer life materials has been desired in an automobile industry. In rubber-made materials, antioxidants have been so far added into rubbers to cope with these requirements for high temperature resistance and for longer life materials. However, almost all antioxidants available in these days have been developed for adding mainly into SBR rubber tires or for various plastics materials. These materials are usually used at a temperature of from about 100 to 150° C., so it is sufficient that the antioxidants used in these materials have a temperature resistance of up to about 150° C., and there have been almost no antioxidant that is assumed to be used at a temperature higher than 150° C. Accordingly, when these antioxidants are used at a temperature higher than 150° C., these antioxidants are apt to volatile from the surface of the materials making it difficult to prolong the life of the materials.

To avoid such a fault and to make an antioxidant less volatile, increasing the molecular weight of antioxidnats has been studied. Some of the commercially available antioxidants at present are considerably less volatile. However, in such a less volatile antioxidant, the dispersibility of the antioxidant in a rubber is lowered owing to the increase of its molecular weight. Also, to realize the low volatility of an antioxidant, an attempt of chemically bonding the antioxidant molecule to a polymer and an attempt of holding the antioxidant to a porous substance have been carried out, but there have been many problems in practical use of these methods and the above-described attempts have not yet been practically used at present.

In particular, in the case of an acrylic rubber, an antioxidant is incorporated into the rubber for the purpose of prolonging the life thereof but the antioxidants proposed until now are yet insufficient and a more improvement has been desired.

In order to make an antioxidant function for a long period of time, it is necessary that the antioxidant must be remained in a rubber for a long period of time and also it is necessary that the antioxidant that traps a radical therein is stable. To hold an antioxidant in a rubber for a long period of time, an attempt of increasing the molecular weight of the antioxidant, an attempt of bonding the antioxidant to a polymer, etc., have been practiced until now as described above, but in the case of using an antioxidant for an acrylic rubber, in particular for an acrylic rubber as a sealing material, such attempts have not sufficiently been able to give a good result and as the case may be, on the contrary, hasten aging.

In general, aging of a rubber is caused by an oxidation reaction and the oxidation is supposed to be more severe at the surface of the rubber, the molecule of the antioxidant is required to have a moderate mobility toward the rubber surface from inner part of the rubber. However, with increasing the molecular weight of an antioxidant and by bonding an antioxidant to a polymer, the mobility of the antioxidant in the rubber becomes small, which is considered to be the reason that the desired effect is not obtained. Also, in such an antioxidant, it is considered that the radical-trapping capacity per parts by weight of the antioxidant is lowered owing to the increase of the molecular weight of the antioxidant.

On the contrary, when an antioxidant having a relatively low molecular weight and a high mobility in the rubber is used, although the antioxidant has a sufficient mobility in the system and a high radical-trapping capacity per weight parts of the antioxidant, the volatile loss of the antioxidant from the surface of the system or the extraction of the antioxidant from the surface of the system into a contact medium, etc., is large, whereby the sufficient effect cannot be obtained.

Furthermore, it has been performed to improve the heat resistance by combination of plural antioxidants, such as the combination of a primary antioxidant (radical-trapping agent such as an amine based or phenol based antioxidant, etc.) and a secondary antioxidant (peroxide decomposing agent such as a sulfur based or phosphorus based antioxidant, etc.), but in this case, the function and the object of each antioxidant are utterly different.

Also, there is a related art that describes combination of a same kind of antioxidants, the use thereof is not limited to one kind. It describes that antioxidants each having the same performance can be used together, but there is no suggestion on a synergistic effect by combinaion of them.

In a chloroprene rubber and NBR, as the case may be, the synergistic effect is obtained by combination of amine based antioxidants, but the combination of the amine based antioxidants in the above-described case is not effective in the case of acrylic rubbers. The reason is as follows. That is, because the acrylic rubbers are required to be used at a higher temperature (about 150° C.) than the temperature at which the chloroprene rubbers and NBR are used, and also become hard when heat degradation occurs, there is a fact that conventional antioxidants cannot endure the practical use at such a high temperature.

SUMMARY OF THE INVENTION

An object of the present invention is to provide a phenylenediamine derivative effectively used as an antioxidant which have a property of less volatility and almost no thermal degradation under a high-temperature condition higher than 150° C.

Also, another object of the present invention is to provide a process for manufacturing the phenylenediamine derivative mentioned above.

And also, another object of the present invention is to provide an antioxidant for acrylic rubber, which can sufficiently attain an aging preventing action at a higher temperature than a temperature required for acrylic rubbers by the synergistic effect with combination of the same kind of antioxidant.

The above-described objects are achieved by a phenylenediamine derivative represented by the following formula (I):

(I)

wherein $R_1$ and $R_2$ each represents a hydrogen atom, a lower alkyl group, or a lower alkoxy group; $R_3$ represents a hydrogen atom or a methyl group; $R_4$ represents a methyl group or an ethyl group; and n and m are an integer of 1, 2, or 3.

Also, the above-described objects are further acieved by a phenylenediamine derivative represented by the following formula (II):

(II)

wherein $R_1$ and $R_2$ each represents a hydrogen atom, a lower alkyl group, a lower alkoxy group, or a cyano group; and n and m are an intger of 1, 2, or 3.

Furthermore, the above-described objects are achieved by an antioxidant for acrylic rubber having a mixture of:

(A) an antioxidant compound represented by the following formula:

(A₁)

(A₂)

(A₃)

wherein $R_1$ represents a hydrogen atom or an alkyl group; $R_2$ represents an alkyl group or a cumyl group; and $R_3$ represents an alkyl group, and (B) an antioxidant compound represented by the following formula:

(B₁)

(B₂)

DETAILED DESCRIPTION OF THE INVENTION

Then, the present invention will be described in detail.

The above-described phenylenediamine derivative represented by the formula (I) [hereinafter referred to as the phenylenediamine derivative (I)] is produced by reacting N,N'-diphenyl-1,4-phenylenediamine with a styrene (or styrene derivative) represented by the following formula:

wherein $R_1$ and $R_2$ each represents a hydrogen atom, a lower alkyl group, or a lower alkoxy group; and $R_3$ and $R_5$ each represents a hydrogen atom or a methyl group, in the presence of a protonic acid catalyst.

The styrene (or styrene derivative) represented by the above-described formula includes 4-(1-propenyl)-1,2-dimethoxybenzene, 4-(1-propenyl)methoxybenzene, tert-butylstyrene, α-methylstyrene, styrene, etc., and they may be used singly or as a mixture of them.

The reaction of both compounds is carried out using N,N'-diphenyl-1,4-phenylenediamine and the styrene (or styrene derivative) in a molar ratio of 1 to not less than 2, in the presence of a protonic acid catalyst such as concentrated sulfuric acid, phosphoric acid, etc., at a reaction temperature of from about 100 to 200° C., preferably from about 130 to 160° C.

As the reaction solvent, preferably an aromatic hydrocarbon such as benzene, toluene, xylene, etc., or an aliphatic hydrocarbon , etc., but the reaction can be carried out under non-solvent system. Because the reaction is one kind of a Friedel-Crafts reaction, the reaction in the presence of an aluminum chloride catalyst, which is, as a matter of course, used as the reaction catalyst, may be considered but in this case, the unreacted raw material (i.e., N,N'-diphenyl-1,4-phenylenediamine) cannot effectively be separated after the reaction.

The reaction product obtained contains a slight amount of a mono-substituted product but the reaction product has almost the desired di-substituted product or the poly-substituted product. When a mixture of two or more kinds of the styrene derivatives is used, the substituents $R_1$ to $R_4$ of the di-substituted product or the poly-substituted product can be different from each other. Also, when n and m each is 1, the substitution position is generally at the para-position to the —NH— group and when n and m each is 2 (or 3), the substitution positions are at the ortho-position (and ortho'-position) in addition to the para-position to the —NH— group.

The phenylenediamine derivative (I) made up of such a di-substituted product or poly-substituted product can be effectively used as an antioxidant for rubber, which is used under a high-temperature condition of about 150° C. or higher. The phenylenediamine derivative (I) has a feature that the number average molecular weight Mn of not less than about 400 and the weight loss when it is allowed to stand for 40 hours in hot air of 175° C. is in the range of about 30% or lower, preferably about 10% or lower. Also, when the phenylenediamine derivative (I) is added to a sealing material, which is brought into contact with an engine oil, such as an oil seal, an O-ring, a packing, etc., it has also a feature of being excellent in the oil-extraction resistance.

Accordingly, the phenylenediamine derivative (I) of the present invention can be effectively used as an antioxidant for various rubbers having various kinds of crosslinking groups, such as acrylic rubbers, NBR, SBR, EPDM, etc. The amount of antioxidant in the rubber composition is within the range from about 0.1 to 10 parts by weight, preferably from about 0.3 to 5 parts by weight, per 100 parts by weight of the rubber.

Also, the phenylenediamine derivative (I) can be, as a matter of course, used in combination with other antioxidant.

The above-described phenylenediamine derivative of the present invention represented by the formula (II) [hereinafter referred to as the phenylenediamine derivative (II)] is produced by reacting N,N'-diphenyl-1,4-phenylenediamine with a benzoyl chloride (or benzoyl chloride derivatives) represented by the following formula:

wherein $R_1$ and $R_2$ each represents a hydrogen atom, a lower alkyl group, a lower alkoxy group, or a cyano group; and X represents a halogen atom.

The benzoyl chloride (or its derivatives) shown by the above-described formula includes not only benzoyl chloride but also its 4-methyl derivative, 4-methoxy derivative, and 4-cyano derivative, etc. These reagents can be used singly or as a mixture thereof.

The reaction of both the compounds described above is carried out by using N,N'-diphenyl-1,4-phenylenediamine and the benzoyl chloride (or its derivatives) shown by the above formula in a molar ratio of 1 to not less than 2 mole, under the presence of an anhydrous aluminum chloride catalyst, at a reaction temperature of from about 30 to 100° C., preferably from about 40 to 80° C. As a reaction solvent, an aromatic hydrocarbon such as benzene, toluene, xylene, etc., or an aliphatic hydrocarbon, etc., are preferably used, but the reaction can be carried out under non-solvent system.

The reaction product obtained contains a slight amount of a mono-substituted product but the reaction product has almost the desired di-substituted product or the poly-substituted product. When a mixture of two or more kinds of the styrene derivatives is used, the substituents $R_1$ and $R_2$ of the di-substituted product or the poly-substituted product can be different from each other. Also, when n and m each is 1, the substitution position is generally at the p-position to the —NH— group and when n and m each is 2 (or 3), the substitution positions are at the o-position (and o'-position) in addition to the p-position to the —NH— group.

The phenylenediamine derivative (II) made up of such a di-substituted product or poly-substituted product can be effectively used as an antioxidant for rubber, which is used under a high-temperature condition of about 150° C. or higher. The phenylenediamine derivative (II) has a feature that the number average molecular weight Mn of not less than about 450 and the weight loss when it is allowed to stand for 40 hours in hot air of 175° C. is in the range of about 40% or lower, preferably about 20% or lower. Also, when the phenylenediamine derivative (II) is added to a sealing material, which is brought into contact with an engine oil, such as an oil seal, an O-ring, a packing, etc., it has also a feature of being excellent in the oil-extraction resistance.

Accordingly, the phenylenediamine derivative (II) of the present invention can be effectively used as an antioxidant for various rubbers having various kinds of crosslinking groups, such as acrylic rubbers, NBR, SBR, EPDM, etc. The amount of the antioxidant in the rubber is from about 0.1 to 10 parts by weight, preferably from about 0.3 to 5 parts by weight, per 100 parts by weight of the rubber.

Also, the phenylenediamine derivative (II) can be, as a matter of course, used together with other antioxidant.

Then, the antioxidant for acrylic rubber made up of a mixture of antioxidant compounds will be described in detail.

As an aspect of the present invention, the antioxidant for acrylic rubber of the present invention is made up of a mixture of (A) an antioxidant compound [hereinafter referred to as the antioxidant (A) or the antioxidant compound (A)] represented by the formula ($A_1$), ($A_2$), or ($A_3$) and (B) an antioxidant compound [hereinafter, is referred to as the antioxidant (B) or the antioxidant compound (B)] represented by the formula ($B_1$) or ($B_2$) as described above.

The antioxidant A has a property of relatively easily mobility in rubber. The antioxidant corresponding to the formula ($A_1$) includes an alkylated diphenylamine (Nocrac ODA, AD-F, trade names, made by Ouchi Shinko Kagaku K.K.), etc., and the antioxidant corresponding to the formula ($A_2$) includes N-phenyl-N'-isopropyl-p-phenylenediamine (Nocrac 810-NA, a trade name made by the above-described company), N-phenyl-N'-(1,3-dimethylbutyl)-p-phenylenediamine (Nocrac 6C, a trade name made by the above-described company), etc. Also, the antioxidant corresponding to the formula ($A_3$) is obtained by reacting N,N'-diphenyl-1,4-diphenylenediamine with an equimolar amount of α-methylstyrene in the presence of a protonic acid catalyst as shown in Reference Example 2 described below.

On the other hand, the antioxidant B has a property of less volatility as compared with the antioxidant A. And when rubber articles are used in contact with oil fluid or the like, anti-extracting property to the fluid is also required. So the chemical structure of this type of antioxidant is limited to have a diphenylamine structure or an N,N'-diphenyl-p-phenylenediamine structure and further is limited to have a cumyl group at the end of the aromatic ring of the diphenylamine structure or the N,N'-diphenyl-p-phenylenediamine structure. The reason of limiting the structure of the antioxidant B as described above is that in addition of the effect of reducing the volatility and the extraction loss of the antioxidant by means of increasing the molecular weight, the stability of the antioxidant after trapping radicals is improved by the steric hindrance of the cumyl group.

The antioxidant corresponding to the formula ($B_1$) described above includes 4,4'-bis($\alpha,\alpha$-dimethylbenzyl) diphenyl (Nocrac CD, a trade name made by Ouchi Shinko Kagaku K.K.), etc., and the antioxidant corresponding to the formula ($B_2$) includes the compound obtained by reacting N,N'-diphenyl-1,4-diphenylenediamine with $\alpha$-methylstyrene in a molar ratio of 1 to not less than 2 mole in the presence of a protonic acid catalyst (see Japanese Patent Application No. 9-24460).

These antioxidant compound (A) and antioxidant compound (B) are used at a ratio of from 4 to 40% by weight, preferably from 6 to 30% by weight for the compound (A) and from 96 to 60% by weight, preferably from 94 to 70% by weight for the compound (B), respectively. When the amount of the antioxidant compound (A) is less than the above ratio, accordingly the antioxidant compound (B) is used at a ratio more than the above ratio, the initial anti-aging property becomes insufficient. On the other hand, when the antioxidant compound (A) is more than the above ratio, accordingly the antioxidant compound (B) is used at a ratio less than the above ratio, the long term anti-aging property becomes insufficient.

The sum total of the antioxidant compounds (A) and (B) for acrylic rubber is in the range of about 0.2 to 10 parts by weight, preferably from about 0.5 to 6 parts by weight, per 100 parts by weight of the acrylic rubber.

The acrylic rubber containing two kinds of the above-described antioxidant compounds (A) and (B) is further properly compounded with a reinforcing agent or a filler, such as carbon black, silica, etc.; a lubricant such as stearic acid, etc.; a crosslinking agent; a crosslinking accelerator, etc., and is vulcanized according to an ordinary curing condition.

[Effect of the Invention]

According the present invention, the phenylenediamine derivatives (I) and (II) have an excellent in the dispersability into rubbers and in the thermal stability even in the case of being used under a high-temperature condition. So the antioxidants of the present invention can be effectively used as antioxidants for rubbers, etc.

The phenylenediamine derivatives (I) and (II) have also an excellent property in the point of the oil-extraction resistance even in the case of being added to a sealing material which is brought into contact with an engine oil, so these phenylenediamine derivatives can be effectively used in sealing materials such as oil seals, O-rings, packings, etc.

Also, when the antioxidant made up of a combination of the same kinds of the antioxidants, namely (A) and (B), of the present invention is added to an acrylic rubber and vulcanized, due to the synergetic action of the combined antioxidants, the excellent heat aging resistance can be imparted to vulcanized acrylic rubber products, which is used at a high temperature, such as oil seals, O-rings, etc., for a long period of time.

The following Examples are intended to illustrate the present invention more practically but not to limit the invention in any way.

EXAMPLE 1

(Production of Antioxidant 1)

In a 500 ml three-necked flask on an oil bath were placed 52.0 g of N,N'-diphenyl-1,4-phenylenediamine (Nocrac DP, a trade name made by Ouchi Shinko Kagaku K.K.) and 74.9 g of 4-(1-propenyl)-1,2-dimethoxybenzene and after sufficiently replacing the atmosphere with a nitrogen gas with stirring, the temperature of the oil bath was increased to 140° C. Thereafter, 5 g of concentrated sulfuric acid was added dropwise from a dropping funnel to the mixture over a period of about 30 minutes, and when after finishing the addition, the reaction was further continued for about 15 hours, the viscosity of the reaction mixture was increased with the passage of time. After the reaction was over, toluene was added to the reaction mixture to form a toluene solution, then the toluene solution was poured into an excessive amount of an aqueous sodium hydroxide solution, followed by stirring, and then a lower layer (aqueous solution layer) formed was separated by a separating funnel. The toluene solution layer obtained was washed with water several times until the solution became neutral. Finally, the supernatant liquid was evaporated off to provide 92.5 g (yield 75%) of a blackish brown desired product.

A definite amount of the product obtained was allowed to stand in an air-circulation type oven at 175° C. for 40 hours but in this case, the weight loss was lower than 5% (3.2%). Also, when the product obtained was analyzed by a TLC method (using a silica gel plate, development solvent: n-hexane/toluene=1/2 by volume), the raw material components remained were not confirmed and although the spot of an impurity which was considered to be the mono-substituted product and spots of unknown structures existed slightly, the greater part of the product was the desired product.

Mn (by a GPC method using tetrahydrofuran as the solvent): 860

Figure 1:
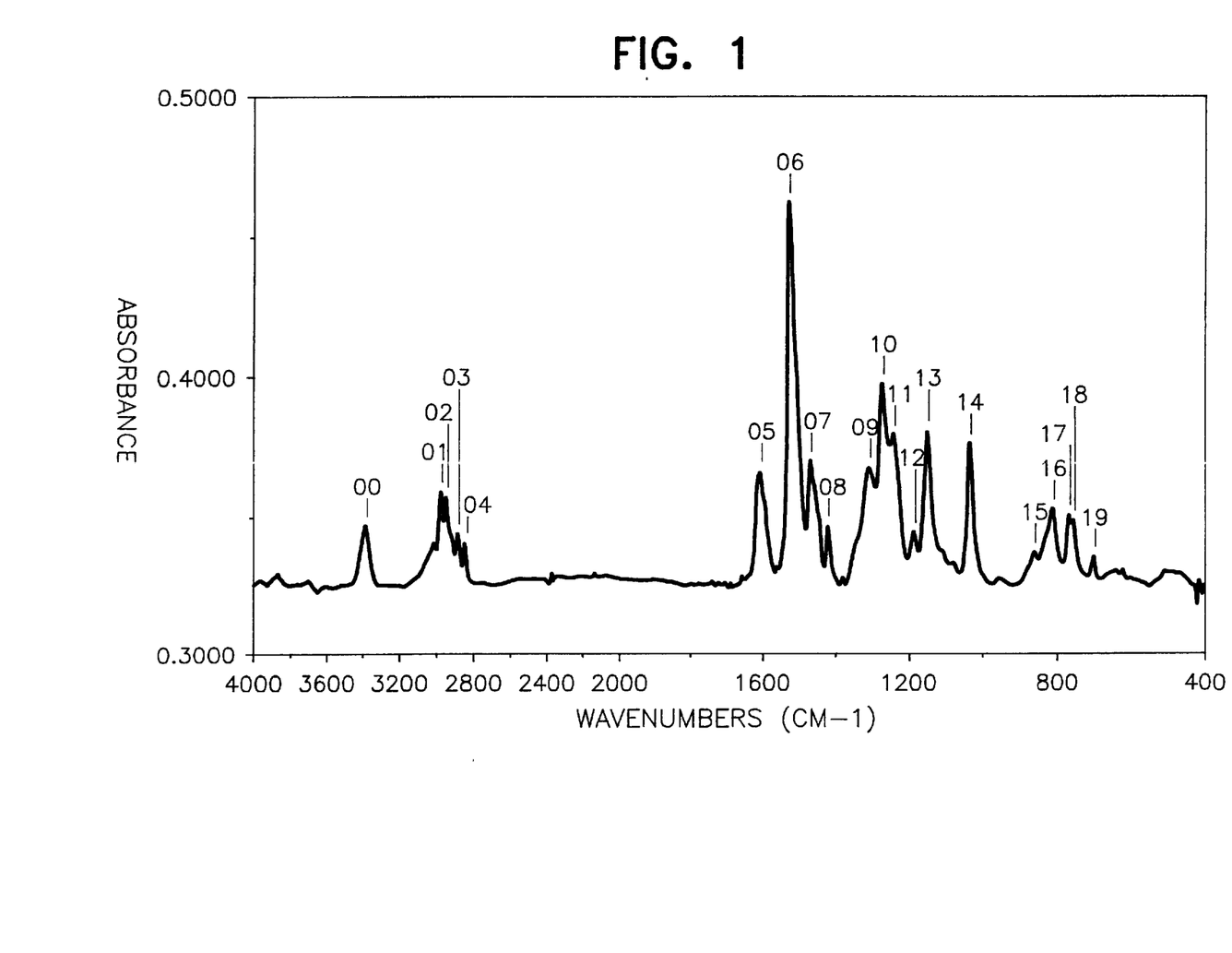
FIG. 1 is a graph showing the infrared absorption spectrum of the antioxidant 1.

FI-IR (measured by casting on a KRS-5 crystal plate): FIG. 1

$^1$H-NMR (CDCl$_3$, 25° C.):

near 0.9 ppm (CH$_3$ group)

near 3.8 ppm (OCH$_3$ group)

near 6.7 to 7.2 ppm (aromatic H)

Presumed Structure

EXAMPLE 2

(Production of Antioxidant 2)

By following the same procedure as in Example 1 except that the amount of N,N'-diphenyl-1,4-phenylenediamine was changed to 78.0 g and 99.5 g of 4-tert-butylstyrene was used in place of the 4-(1-propenyl)-1,2-dimethoxybenzene, 139.0 g (yield 80%) of the desired product was obtained.

The weight loss of the product at 175° C. for 40 hours was lower than 10% (6.2%) and the behaviors of the product by the TLC method were substantially the same as those in Example 1.

Mn (by a GPC method using tetrahydrofuran as the solvent): 700

Figure 2:
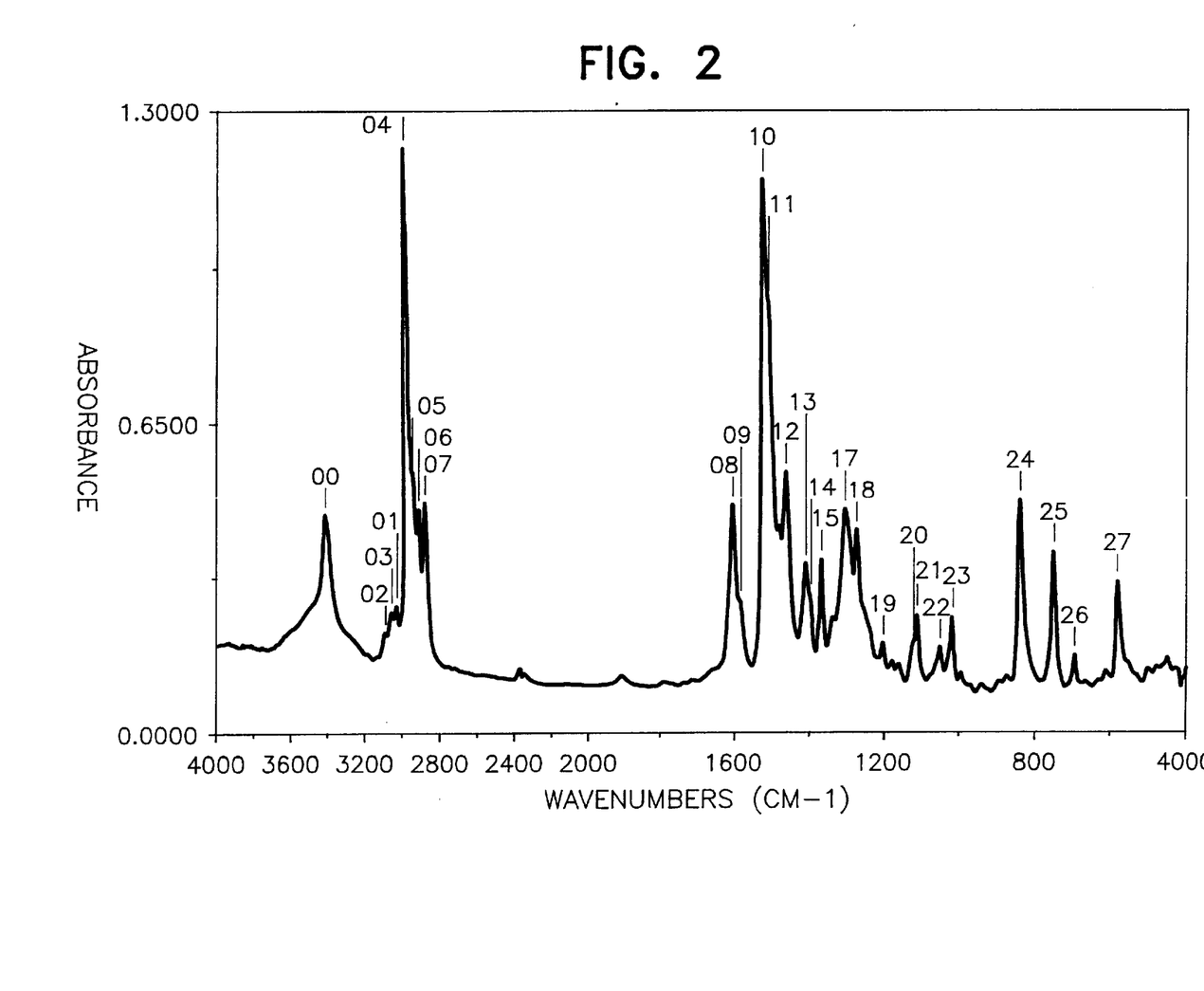
FIG. 2 is a graph showing the infrared absorption spectrum of the antioxidant 2.

FI-IR (measured by casting on a KRS-5 crystal plate): FIG. 2

$^1$H-NMR (CDCl$_3$, 25° C.):

near 1.22 ppm (CH$_3$ group)

near 7.1 ppm (aromatic H)

Presumed Structure

EXAMPLE 3
(Production of Antioxidant 3)

By following the same procedure as in Example 1 except that 62.2 g of anethol-(p-methoxypropenylbenzene) was used in place of the 4-(1-propenyl)-1,2-dimethoxybenzene, 94.6 g (yield 85%) of a blackish brown desired product was obtained.

The weight loss of the product at 175° C. for 40 hours was lower than 10% (8.6%) and the behaviors of the product by the TLC method were substantially the same as those in Example 1.

Mn (by a GPC method using tetrahydrofuran as the solvent): 704

Figure 3:
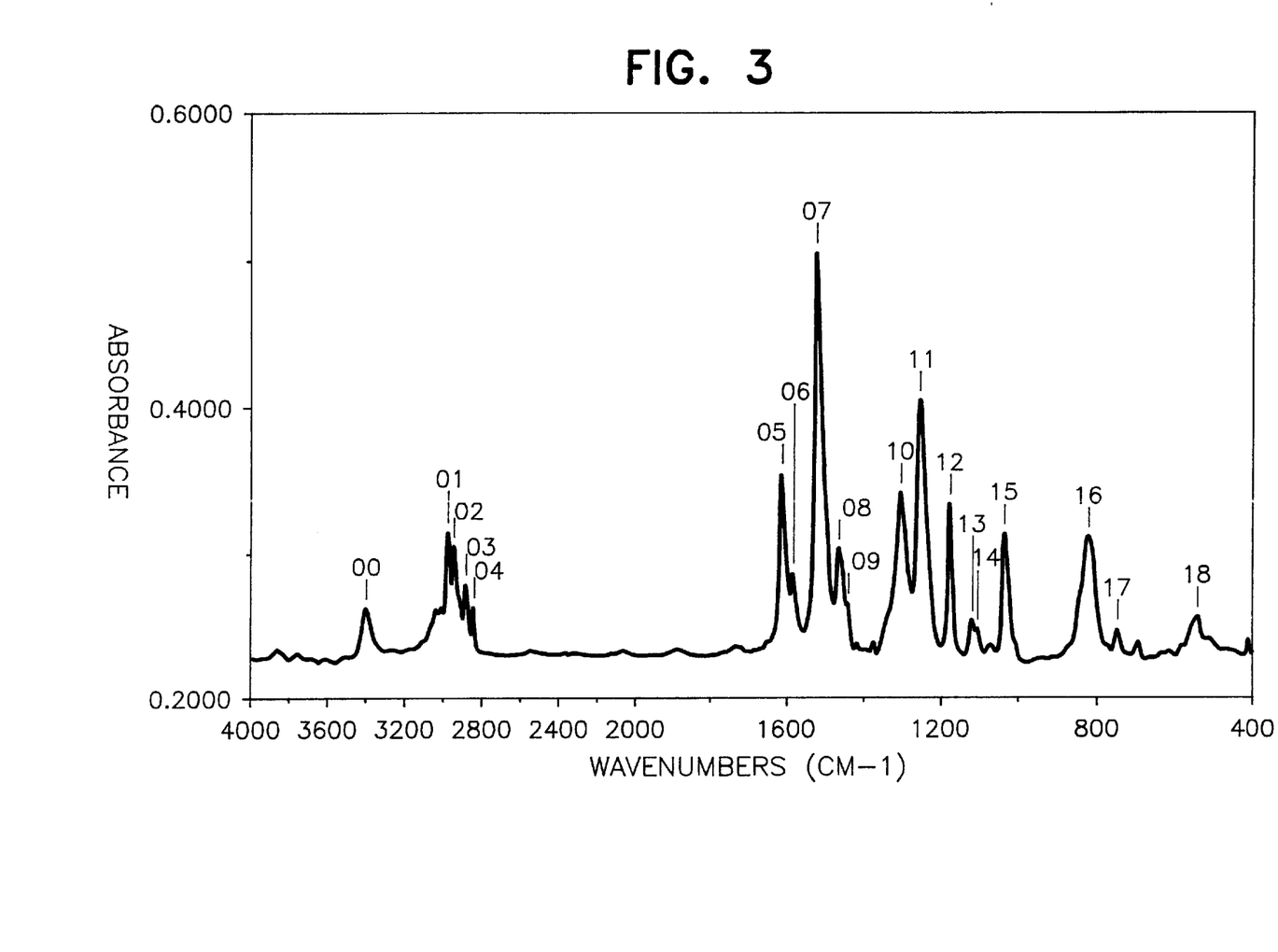
FIG. 3 is a graph showing the infrared absorption spectrum of the antioxidant 3.

FI-IR (measured by casting on a KRS-5 crystal plate): FIG. 3

$^1$H-NMR (CDCl$_3$, 25° C.):

near 0.88 ppm (CH$_3$ group)

near 3.8 ppm (OCH$_3$ group)

near 6.8 to 7.2 ppm (aromatic H)

Presumed Structure

EXAMPLE 4
(Production of Antioxidant 4)

By following the same procedure as in Example 1 except that 76.0 g of α-methylstyrene was used in place of the 4-(1-propenyl)-1,2-dimethoxybenzene, 84.6 g (yield 85%) of a blackish brown desired product was obtained.

The weight loss of the product at 175° C. for 40 hours was lower than 10% (8.2%) and the behaviors of the product by the TLC method were substantially the same as those in Example 1.

Mn (by a GPC method using tetrahydrofuran as the solvent): 500

Figure 4:
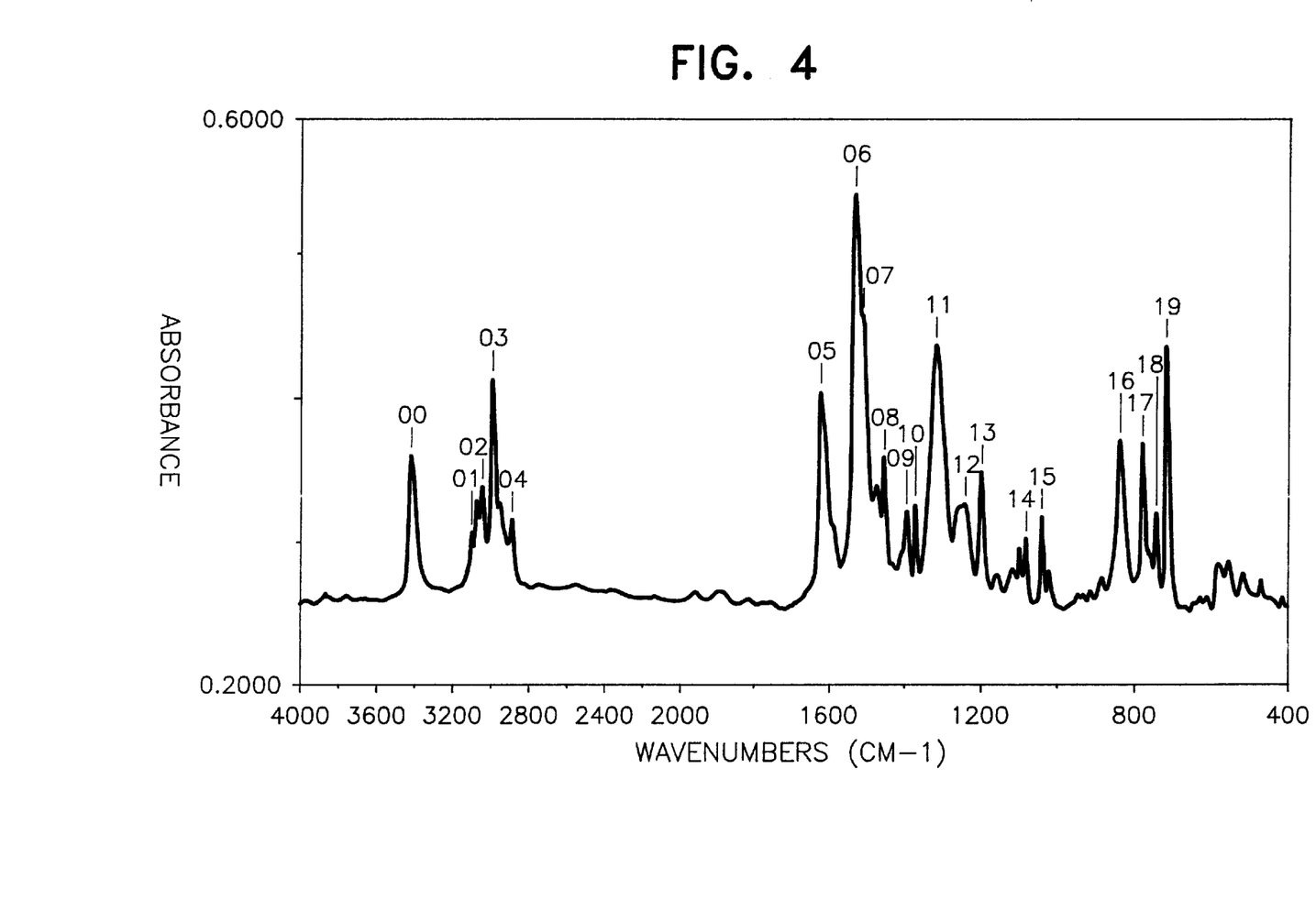
FIG. 4 is a graph showing the infrared absorption spectrum of the antioxidant 4.

FI-IR (measured by casting on a KRS-5 crystal plate): FIG. 4

$^1$H-NMR (CDCl$_3$, 25° C.):

near 1.6 ppm (CH$_3$ group)

near 6.7 to 7.3 ppm (aromatic H)

Presumed Structure

Comparative Example 1

When in Example 4, an aluminum chloride catalyst was used in place of the concentrated sulfuric acid catalyst, 30% or more of the raw material, N,N'-diphenyl-1,4-phenylenediamine, remained in the reaction mixture and it was difficult to remove the remained raw material by a purification method.

EXAMPLES 5 to 8 and

Comparative Examples 2 and 3

|  | (parts by weight) |
|---|---|
| Chlorine-containing acrylic rubber (Noxtite PA404K, a trade name made by Nippon Mektron Ltd.) | 100 |
| HAF Carbon black | 60 |

-continued

|  | (parts by weight) |
|---|---|
| Stearic acid | 1 |
| Antioxidant (shown below) | 2 |
| Sodium stearate (NS Soap, a trade name made by Kao Corporation) | 0.25 |
| Potassium stearate (Nonsoul SK-1, a trade name made by NOF Corporation) | 0.25 |
| Sulfur | 0.2 |

The antioxidant used in each of Examples and Comparative Examples were as follows.

Antioxidant 1 (Example 5)

Antioxidant 2 (Example 6)

Antioxidant 3 (Example 7)

Antioxidant 4 (Example 8)

Antioxidant 5[*1] (Comparative Example 2)

Antioxidant 6[*2] (Comparative Example 3)
Note): Antioxidant 5: Nocrac CD, a trade name made by Ouchi Shinko Kagaku K.K.; weight loss at 175° C. for 40 hours: about 35%
Presumed Structure Antioxidant 6: Nocrac DP; weight loss at 175° C. for 40 hours: about 70%

Each acrylic rubber composition obtained by roll kneading the respective compounding components described above was press-vulcanized (primary vulcanization) at 180° C. for 8 minutes, thereafter, subjected to a secondary vulcanization in a hot air circulating oven at 175° C. for 4 hours, and formed into a sheet form of 120 mm×220 mm×2 mm.

About each test piece thus formed, the normal-state property (according to JIS K-6301) and the compression set (150° C., 70 hours, and 25% compression) were measured and also a heat aging resistance test (measured as the normal state change after 70 hours at 175° C.) was carried out. The results obtained are shown in the following table.

|  | Example | | | | C. Example | |
| --- | --- | --- | --- | --- | --- | --- |
|  | 5 | 6 | 7 | 8 | 2 | 3 |
| [Normal-state property] | | | | | | |
| Hardness (JIS A) | 65 | 64 | 66 | 65 | 64 | 65 |
| Tensile strength (MPa) | 14.6 | 14.3 | 14.8 | 14.3 | 14.2 | 14.4 |
| 100% Modulus (MPa) | 4.9 | 4.6 | 5.0 | 4.9 | 4.7 | 4.8 |
| Elongation (%) | 230 | 240 | 240 | 225 | 230 | 240 |
| [Heat-aging resistance test] | | | | | | |
| Hardness change (point) | +4 | +4 | +5 | +6 | +8 | +11 |
| Change ratio of tensile strength (%) | −10 | −10 | −15 | −16 | −23 | −20 |
| Change ratio of elongation (%) | +2 | +4 | +6 | +8 | +11 | −2 |
| [Compression set] | | | | | | |
| 150° C., 70 hours | 22 | 24 | 25 | 27 | 29 | 32 |

In the above table, C. Example: Comparative Example

From the results of the heat-aging resistance test described above, it can be seen that the samples using the antioxidants of the present invention can improve the heat aging resistance and the compression set characteristics without deteriorating the normal-state property, that is, the results show the effectiveness of the antioxidants of the present invention.

EXAMPLE 9
(Production of Antioxidant 7)

In a 300 ml three-necked flask on an oil bath were placed 5.2 g of N,N'- diphenyl-1,4 -phenylenediamine (Nocrac DP, a trade name made by Ouchi Shinko Kagaku K.K.) and 100 ml of toluene and after sufficiently replacing the atmosphere in the flask with a nitrogen gas, 6.7 g of benzoyl chloride was added dropwise to the mixture from a dropping funnel. Then, after finishing the addition, 6.0 g of anhydrous aluminum chloride was added thereto slowly. After adding the total amount of anhydrous aluminum chloride, the temperature of the oil bath was increased to 80° C. and while trapping hydrogen chloride generated, the reaction was continued for about 15 hours with stirring.

After finishing the reaction, 300 ml of toluene was added to the reaction mixture and thereafter, the content of the flask was poured into 500 ml of distilled water little by little. After adding the total amount of the content, the organic layer of the upper portion was transferred into a 300 ml flask and after adding 100 ml of an aqueous solution of 10% by weight sodium hydroxide to the organic layer, the mixture was refluxed. Thereafter, the organic layer was collected and washed with distilled water using a separating funnel until the liquid became neutral. After washing, toluene was distilled off from the organic layer to provide 4.6 g (yield 49%) of a blackish brown desired product.

A definite amount of the product obtained was allowed to stand in an air-circulation type oven at 175° C. for 40 hours but in this case, the weight loss was lower than 10% (7.8%). Also, when the product obtained was analyzed by a TLC method (using a silica gel plate, development solvent: n-hexane/toluene=1/2 by volume), the raw material components remained were not confirmed and although the spot of an impurity which was considered to be the-mono-substituted product and spots of unknown structures existed slightly, the greater part of the product was the desired product.

Mn (by a GPC method using tetrahydrofuran as the solvent): 468.56

FI-IR (measured by casting on a KRS-5 crystal plate):

| | |
| --- | --- |
| 3342 cm$^{-1}$ | N—H stretching vibration |
| 3060 cm$^{-1}$ | aromatic C—H stretching vibration |
| 1649 cm$^{-1}$ | C=O stretching vibration |
| 1300 to 1600 cm$^{-1}$ | vibration originated from aromatic ring |
| near 700 cm$^{-1}$ | vibration originated from aromatic ring |

Presumed Structure

EXAMPLE 10
(Production of Antioxidant 8)

By following the same procedure as in Example 9 using 7.5 g of 4-cyanobenzoyl chloride in place of benzoyl chloride, 7.1 g (yield 68%) of a blackish brown desired product was obtained.

The weight loss of the product at 175° C. for 40 hours was lower than 20% (19.9%) and the behaviors by the TLC method were substantially the same as those in Example 9.

Mn (by a GPC method using tetrahydrofuran as the solvent): 518.58

FI-IR (measured by casting on a KRS-5 crystal plate):

| | |
|---|---|
| 3388 cm$^{-1}$ | N—H stretching vibration |
| 3043 cm$^{-1}$ | aromatic C—H stretching vibration |
| 2229 cm$^{-1}$ | C≡N stretching vibration |
| 1651 cm$^{-1}$ | C=O stretching vibration |
| 1280 to 1600 cm$^{-1}$ | vibration originated from aromatic ring |
| near 700 cm$^{-1}$ | vibration originated from aromatic ring |

Presumed Structure

EXAMPLE 11
(Production of Antioxidant 9)

In a 300 ml three-necked flask equipped with a reflux condenser on an oil bath were placed 9.2 g of p-anisic acid (p-methoxybenzoic acid) and 100 ml of diisopropyl ether and after stirring the mixture, 18.0 g of thionyl chloride was added dropwise to the mixture from a dropping funnel. Thereafter, the oil bath was heated and the resultant mixture was refluxed for 2 hours. The reflux condenser was removed and the flask was heated under a reduced pressure to completely remove volatile components.

After returning the pressure in the flask in which p-anisic acid chloride remained to the atmospheric pressure, 7.2 g of N,N'-diphenyl-1,4-phenylenediamine and 100 ml of toluene were added thereto, and then by treating the mixture as in Example 9, 7.8 g (yield 37%) of a blackish brown desired product was obtained.

The weight loss of the product at 175° C. for 40 hours was lower than 15% (14.7%) and the behaviors by the TLC method were substantially the same as those in Example 9.

Mn (by a GPC method using tetrahydrofuran as the solvent): 528.61

FI-IR (measured by casting on a KRS-5 crystal plate):

| | |
|---|---|
| 3327 cm$^{-1}$ | N—H stretching vibration |
| 3031 cm$^{-1}$ | aromatic C—H stretching vibration |
| 2836 cm$^{-1}$ | CH$_3$O group C—H stretching vibration |
| 1651 cm$^{-1}$ | C=O stretching vibration |
| 1300 to 1600 cm$^{-1}$ | vibration originated from aromatic ring |
| 700 cm$^{-1}$ | vibration originated from aromatic ring |

Presumed Structure

EXAMPLES 12 to 14
and

Comparative Examples 4 and 5

| | (parts by weight) |
|---|---|
| Chlorine-containing acrylic rubber (Noxtite PA404K, a trade name made by Nippon Mektron Ltd.) | 100 |
| HAF Carbon black | 60 |
| Stearic acid | 1 |
| Antioxidant (shown below) | 2 |
| Sodium stearate (NS Soap, a trade name made by Kao Corporation) | 2 |
| Potassium stearate (Nonsoul SK-1, a trade | 0.25 |

-continued

| | (parts by weight) |
|---|---|
| name made by NOF Corporation) | |
| Sulfur | 0.2 |

The antioxidant used in each of Examples and Comparative Examples were as follows.

Antioxidant 7 (Example 12)
Antioxidant 8 (Example 13)
Antioxidant 9 (Example 14)
Antioxidant 5*$^1$ (Comparative Example 4)
Antioxidant 6*$^2$ (Comparative Example 5)

Note): Antioxidant 5: Nocrac CD, a trade name made by Ouchi Shinko Kagaku K.K.; weight loss at 175° C. for 40 hours: about 35%

Antioxidant 6: Nocrac DP weight loss at 175° C. for 40 hours: about 70%

Each acrylic rubber composition obtained by roll kneading each compounding components described above was press-vulcanized (primary vulcanization) at 180° C. for 8 minutes, thereafter, subjected to a secondary vulcanization in a hot air circulating oven at 175° C. for 4 hours, and formed into a sheet form of 120 mm×220 mm×2 mm.

About each test piece thus formed, the normal-state property (according to JIS K-6301) and the compression set (150° C., 70 hours, and 25% compression) were measured and also a heat aging resistance test (measured as the normal state change after 70 hours at 175° C.) was carried out. The results obtained are shown in the following table.

|  | Example | | | C. Example | |
|---|---|---|---|---|---|
|  | 12 | 13 | 14 | 4 | 5 |
| [Normal-state property] | | | | | |
| Hardness (JIS A) | 65 | 64 | 66 | 64 | 65 |
| Tensile strength (MPa) | 14.6 | 14.3 | 14.8 | 14.2 | 14.4 |
| 100% Modulus (MPa) | 5.0 | 4.6 | 4.9 | 4.7 | 4.8 |
| Elongation (%) | 230 | 240 | 240 | 230 | 240 |
| [Heat-aging resistance test] | | | | | |
| Hardness change (point) | +5 | +5 | +5 | +8 | +11 |
| Change ratio of tensile strength (%) | −12 | −14 | −14 | −23 | −20 |
| Change ratio of elongation (%) | +1 | +5 | +6 | +11 | −2 |
| [Compression set] | | | | | |
| 150° C., 70 hours | 25 | 24 | 22 | 29 | 32 |

In the above table, C. Example: Comparative Example

From the results of the heat-aging resistance test described above, it can be seen that the samples using the antioxidants of the present invention can improve the heat aging resistance and the compression set characteristics without deteriorating the normal-state property, that is, the results show the effectiveness of the antioxidants of the present invention.

Reference Example 1
(Synthesis of Antioxidant $B_2$)

In a 500 ml three-necked flask on an oil bath were placed 78.0 g (0.3 mol) of N,N'-diphenyl-1,4-diphenylenediamine and 76.0 g (0.64 mol) of α-methylstyrene and after sufficiently replacing the atmosphere in the flask with a nitrogen gas, the temperature of the oil bath was increased to 140° C. Thereafter, 5 g of concentrated sulfuric acid was added dropwise to the mixture from a dropping funnel over a period of 30 minutes and thereafter, the reaction was continued for about 15 hours. In this case, the viscosity of the reaction mixture was increased with the passage of time. After the reaction was over, toluene was added to the reaction mixture obtained to form a toluene solution, thereafter, an excessive amount of an aqueous sodium hydroxide solution was added to the toluene solution, followed by stirring, and a lower layer formed was removed by a separating funnel. The upper layer liquid was washed with water several times until the liquid became neutral and finally the supernatant liquid was evaporated off to provide 126.0 g (yield about 85%) of a blackish brown desired product.

When the product obtained was analyzed by thin layer chromatography, the raw material components were not confirmed and although a spot of an impurity which was considered to be the mono-substituted product existed slightly, the greater part thereof was the desired product.

Infrared absorption spectra (measured by casting on a KRS-5 crystal plate):

| 3400 cm$^{-1}$: | NH group |
|---|---|
| 2966, 2870 cm$^{-1}$: | CH$_3$ group |
| 1610 cm$^{-1}$: | aromatic ring |
| 820 cm$^{-1}$: | aromatic substituted product |

$^1$H-NMR (DMSO, 25° C.)

| 1.6 ppm: | CH$_3$ group |
|---|---|
| 6.7 to 7.3 ppm: | aromatic H |

Reference Example 2
(Synthesis of Antioxidant $A_3$)

By following the same procedure as in Reference Example 1 except for changing the amount of α-methylstyrene to 38.0 g (0.32 mol), 97.5 g (yield 86%) of a blackish brown desired product was obtained. When the product obtained was analyzed by thin layer chromatography, the raw material components were not confirmed and the desired product only was substantially obtained.

Infrared absorption spectra (measured by casting on a KRS-5 crystal plate):

| 3400 cm$^{-1}$: | NH group |
|---|---|
| 2966, 2870 cm$^{-1}$: | CH$_3$ group |
| 1610 cm$^{-1}$: | aromatic ring |
| 820 cm$^{-1}$: | aromatic substituted product |

$^1$H-NMR (DMSO, 25° C.):

| 1.6 ppm: | CH$_3$ group |
|---|---|
| 6.7 to 7.3 ppm: | aromatic H |

EXAMPLE 15

|  | (parts by weight) |
|---|---|
| Acrylic rubber (Noxtite PA404K, a trade name made by Nippon Mektoron K.K.) | 100 |
| HAF Carbon black | 60 |
| Stearic acid | 1 |
| Antioxidant $A_1$ (Nocrac AD-F, a trade name made by Ouchi Shinko Kagaku K.K.) | 1 |
| Antioxidant $B_2$ (synthesized in Reference Example 1) | 2 |
| Sodium stearate (NS Soap, a trade name made by Kao Corporation) | 2 |
| Potassium stearate (Nonsoul SK-1, a trade name made by NOF Corporation) | 0.25 |
| Sulfur | 0.2 |

The components described above were roll-kneaded, the kneaded mixture was press-vulcanized for 8 minutes at 180° C., then oven-vulcanized (secondary vulcanization) for 4 hours at 175° C., and formed into a sheet-form test piece of 120 mm×220 mm×2 mm. About the test piece, the vulcanization property according to JIS K-6301, the heat aging resistance test at 175° C. (measurement of the change of the vulcanized product after 70 hours or after 300 hours), and the compression set (25% compression) were measured.

EXAMPLE$_2$ 16

In Example 15, a combination of 1 part of antioxidant $A_2$ (Nocrac 6C, a trade name made by Ouchi Shinko Kagaku K.K.) and 2 parts of antioxidant $B_1$ (Nocrac CD, a trade name made by the same company as described above) was used.

EXAMPLE 17

In Example 15, a combination of 0.5 part of the antioxidant $A_3$ and 3 parts of the antioxidant $B_2$ was used.

Comparative Example 6

In Example 15, 2 parts of the antioxidant $A_1$ only was used.

Comparative Example 7

In Example 15, 2 parts of the antioxidant $B_2$ only was used.

Comparative Example 8

In Example 15, a combination of 2 parts of the antioxidant $A_1$ and 2 parts of the antioxidant $A_2$ was used.

The measurement results of the samples of the above-described Examples and Comparative Examples are shown in the following table.

|  | Example | | | C. Example | | |
| --- | --- | --- | --- | --- | --- | --- |
|  | 15 | 16 | 17 | 6 | 7 | 8 |
| [Vulcanization property] | | | | | | |
| Hardness (JIS A) | 65 | 64 | 65 | 65 | 64 | 65 |
| 100% Modulus (MPa) | 4.9 | 4.7 | 4.8 | 4.2 | 4.7 | 4.8 |
| Tensile strength (MPa) | 14.3 | 14.2 | 14.8 | 14.0 | 14.2 | 14.0 |
| Elongation (%) | 230 | 230 | 225 | 225 | 230 | 225 |
| [Heat-aging resistance test] (70 hours) | | | | | | |
| Hardness change (point) | +4 | +5 | +4 | +14 | +8 | +12 |
| Change ratio of tensile strength (%) | −11 | −14 | −9 | −28 | −23 | −20 |
| Change ratio of elongation (%) | +6 | +8 | +1 | −20 | +11 | −14 |
| (100 hours) | | | | | | |
| Hardness change (point) | +12 | +16 | +10 | +26 | +20 | +22 |
| [Compression set] | | | | | | |
| 150° C., 70 hours (%) | 22 | 25 | 24 | 28 | 29 | 27 |

In the above table, C. Example: Comparative Example

What is claimed is:

1. A phenylenediamine derivative represented by the following formula (II):

(II)

wherein $R_1$ and $R_2$ each represents a hydrogen atom, a lower alkyl group, a lower alkoxy group, or a cyano group; and n and m each represents 1, 2, or 3.

2. The phenylenediamine derivative of claim 1, wherein the number average molecular weight of the phenylenediamine derivative is at least about 450 and the weight loss thereof when the compound is allowed to stand in hot air of 175° C. is about 40% or less.

3. A method of producing a phenylenediamine derivative represented by the following formula (II):

(II)

wherein $R_1$ and $R_2$ each represents a hydrogen atom, a lower alkyl group, a lower alkoxy group, or a cyano group; and n and m each represents 1, 2, or 3, which comprises reacting N,N'-diphenyl-1,4-phenylenediammine and a benzoyl halide represented by the the following formula:

wherein $R_1$ and $R_2$ each represents a hydrogen, a lower alkyl group, a lower alkoxy group, or a cyano group; and X represents a halogen atom.

4. An antioxidant for rubber comprising a phenylenediamine derivative represented by following formula (II):

(II)

$R_1$ and $R_2$ each represents a hydrogen atom, a lower alkyl group, a lower alkoxy group, or a cyano group; and n and m each represents 1, 2, or 3.

* * * * *